United States Patent [19]
Overman

[11] 4,193,622
[45] Mar. 18, 1980

[54] APPARATUS FOR INSERTING AND REMOVING CONTACT LENSES

[76] Inventor: David C. Overman, 4525 W. Twain Ave., #262, Las Vegas, Nev. 89103

[21] Appl. No.: 915,591

[22] Filed: Jun. 15, 1978

[51] Int. Cl.² .............................................. A61F 9/00
[52] U.S. Cl. .............................................. 294/1 CA
[58] Field of Search .................... 294/1 CA, 64 R; 128/303 R

[56] References Cited

U.S. PATENT DOCUMENTS

| | | | |
|---|---|---|---|
| 3,177,874 | 4/1965 | Spriggs | 294/1 CA X |
| 3,600,028 | 8/1971 | Henning | 294/1 CA |
| 3,697,109 | 10/1972 | Parrent | 294/1 CA |
| 3,910,618 | 10/1975 | Massenz | 294/1 CA |
| 4,026,591 | 5/1977 | Cleaveland | 294/1 CA |
| 4,113,297 | 9/1978 | Quinn | 294/1 CA |

Primary Examiner—Johnny D. Cherry
Attorney, Agent, or Firm—Seiler & Quirk

[57] ABSTRACT

Apparatus for inserting and removing contact lenses has an adjustable horizontal plate for receiving the user's forehead, and for orienting the user's eyes relative to lens holding members. The apparatus has two adjustable pivoted blocks, each having substantially vertical, separate lens-inserting and lens-removing devices which can be selectively rotated into operating position for insertion or removal. The forehead plate is aligned at an angle approximately 3°–10° below horizontal to facilitate insertion and removal.

9 Claims, 7 Drawing Figures

APPARATUS FOR INSERTING AND REMOVING CONTACT LENSES

BACKGROUND OF THE INVENTION

Within the past decade, the use of contact lenses has increased dramatically. Contact lenses are not only now a completely acceptable alternative to conventional frame-type eyeglasses, but many people also regard contact lenses as a preferred alternative because of relative safety and improved cosmetic appearance. With the continuing improvement in lens quality, in addition to a wider public acceptance and willingness to put up with the initial inconvenience of adjusting to the lenses, practioners in the contact lens field have become increasingly skilled and experienced at proper fitting of the lenses. Accordingly, some users will purchase several different pairs of lenses having different colors to enhance their appearance in addition to correcting their vision.

Most users apply the lenses one-at-a-time by placing a wetting solution on the lens, placing the lens on the tip of a finger, and moving the lens toward the eye while holding the eyelids apart with the opposite hand. The lenses are removed by manipulating the eyelids in a manner that will lift the lens away from the eye, thereby releasing the capillary attraction which holds the lens to the eye.

While most contact lens users can insert and remove lenses in accordance with this technique, others have great difficulty in acclimating themselves to placing things on their eyes with their fingers. Others have problems in developing sufficient dexterity to place the lenses on their eyes without damaging or dropping them. Women who use makeup will frequently have small quantities of foreign substances on their hands or near their eyes which may coat the lens, thereby necessitating its removal for cleaning and reinsertion. An especially difficult insertion and removal problem is encountered by older people, especially those who have had cataract surgery, who have unsteady hands.

In recognition of some of the difficulties in applying and removing lenses, the prior art is replete with devices to assist the user in inserting and/or removing lenses. Many of these devices comprise suction cups which communicate with squeeze bulb members to create a slight vacuum in the suction cup to hold the lens in place. The device is then moved toward the eye and, when the lens is nearly in place, the squeeze bulb is actuated to release the lens from the suction cup. These devices are generally handheld small units which are intended for insertion of one lens at a time. Typical examples of such a device are found in Carruthers, U.S. Pat. No. 3,934,914, and Koblar, U.S. Pat. No. 3,129,971. In each case the sides of a flexible tube are squeezed to propel the lens from the suction cup. Devices functioning in the same manner are also disclosed in Hutchison, U.S. Pat. No. 3,304,113, and Drdlik, U.S. Pat. No. 4,071,272. These devices also have a light-carrying tube communicating with the suction cup which illuminates the lens when it is in place, thereby assisting the user in orienting the lens toward the eye. Updegraff, U.S. Pat. No. 3,922,025, discloses a similar device wherein the suction cup communicates through a flexible tube with a mouth piece, so that the user may adjust the pressure at the suction cup by sucking or blowing with his mouth. In Henning, U.S. Pat. No. 3,600,028, a lens inserting and removing device is disclosed wherein a suction creating means at the suction cup operates in response to a slight axial movement of the sleeve supporting the suction cup.

These suction-creating devices have not gained general acceptance with contact lens practioners for various reasons. Some regard these devices as being unsafe, in that if the suction device accidentally contacts the surface of the eye and a vacuum is created, damage could occur to the eye. On the other hand, if the force with which the lens is released is even slightly excessive, such that the lens is propelled into the eye, corneal damage could also result.

Various other devices exist for placement of a lens in the eye which involve simple movement of the device toward the eye. Price, U.S. Pat. No. 4,037,866, and Wagstaff, U.S. Pat. No. 2,924,481 each disclose handheld devices having a suction cup mounted on a slideable plunger which the user can move toward his eye. Massenz, U.S. Pat. No. 3,910,618, and Rinaldy, U.S. Pat. No. 2,919,696, disclose similar devices which also have large resilient cups surrounding the plungers which serve to maintain the eyelids in an open position. Allen, U.S. Pat. No. 3,897,968 discloses a suction cup mounted on a hollow stem which communicates with an aerosol which can cause retention or release of a lens held in the suction cup. All of the aforementioned devices require that the device be moved manually by the user toward the eye. This requires a steady hand and substantial confidence on the part of the user, who normally uses one hand to hold his eyelids apart while moving the device toward his eye. In addition, all of these devices require individual insertion of the lenses, thereby necessitating repetition of the insertion or removal process for each eye. A contact lens insertion device which allows the user to orient his head with respect to lens holding members is disclosed in Parrent, U.S. Pat. No. 3,697,109. In this device, contact lenses are held by surface tension on horizontally extending tubes, and the user brings his eyes into alignment with the tubes while resting his chin on a horizontal plate. The user then slides the tubes toward his eye until contact is made between the lens and the eye. No provision is made for removal of lenses with this device, and the pull of gravity could dislodge one of the lenses from the holding device prior to insertion.

Accordingly, it is an object of the invention to provide an apparatus for insertion or removal of contact lenses with which the lenses can be inserted or removed from both eyes simultaneously. It is another object of the invention to provide a device having adjustable headresting features which allow the user to firmly fix his head relative to the device prior to actuation of the device. It is yet a further object of the invention to provide an apparatus having separate lens holding members for insertion and removal of lenses, moved into or out of position as required.

It is yet a further object of the invention to provide a device for insertion and removal of contact lenses which has minimal potential for misuse or injury, and which is virtually foolproof in its operation. These and other objects of the invention will be clear to those skilled in the art from the following description of a specific embodiment of the invention.

SUMMARY OF THE INVENTION

Apparatus for inserting and removing contact lenses comprises a base, head rest means for orienting the head of the user in a downward facing position above the base, a pair of adjustably mounted lens holding supports, each having separate lens resting means for holding a lens for insertion and lens removing means for removal of the lens.

BRIEF DESCRIPTION OF THE DRAWINGS

The invention is best understood with regard to the drawings in which.

DETAILED DESCRIPTION OF THE INVENTION

Figure 1:
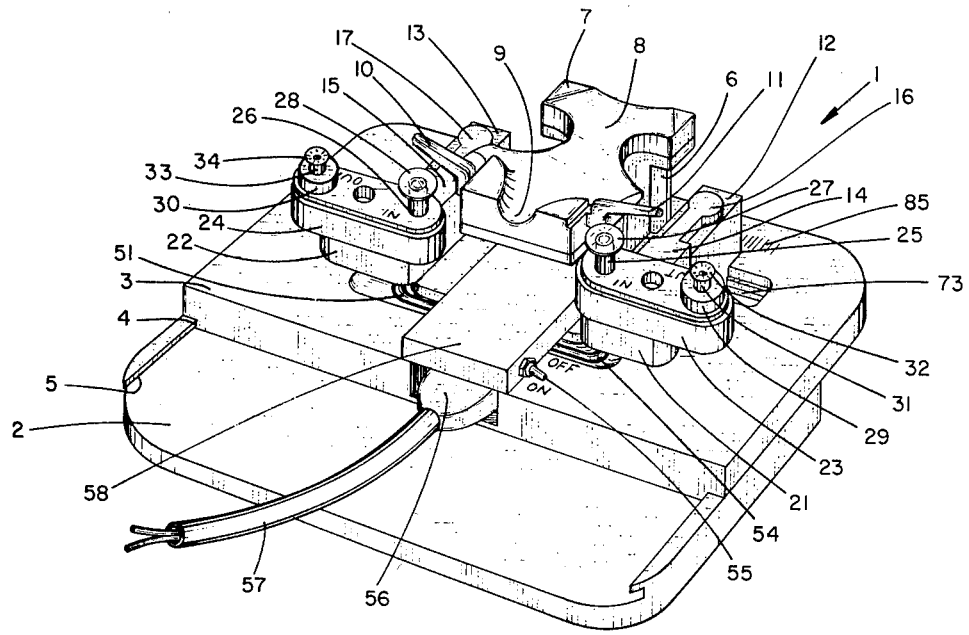
FIG. 1 is a perspective view of the apparatus of the invention.

Referring to FIG. 1, lens insertion and removal device 1 has coextensive, slideably engaged lower and upper base plates 2 and 3, respectively. Rib 4 on the upper base plate slideably engages groove 5 on the bottom plate, allowing adjustment of the base for stability. A substantially vertical member 6 extends upwardly from the middle of the base, and an arm 7 extend forwardly over the base to provide an orientation and resting member for the head of the user. The upper surface 8 of the arm is slightly concave to receive the user's forehead; the forward portion of the arm has a sculptured concave surface 9 for receiving and supporting the bridge of the user's nose. Flanges 10 and 11 extend upwardly and outwardly from arm 7, and serve to open the upper eyelids of the user as his face descends toward the apparatus.

Figure 2:
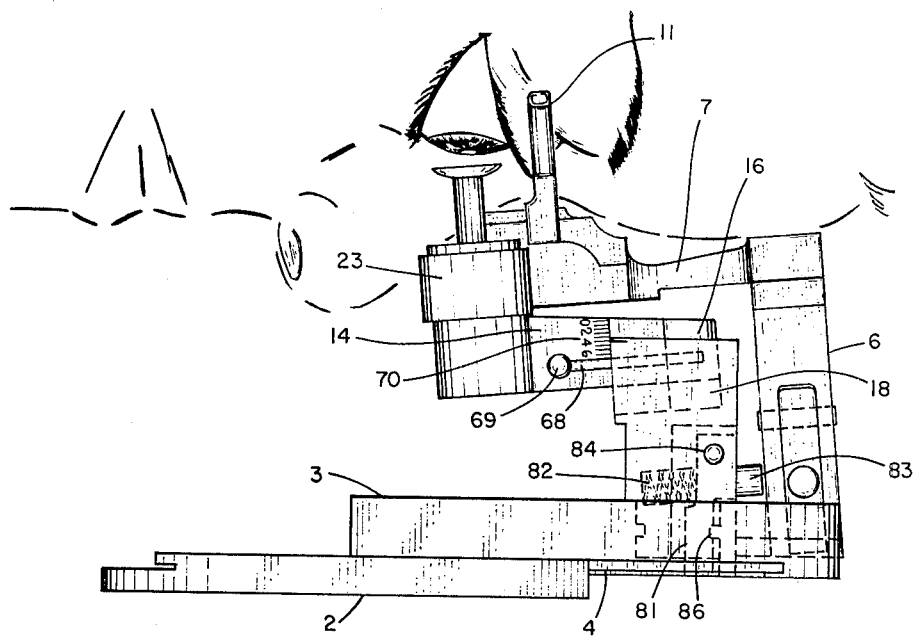
FIG. 2 is a side elevational view of the apparatus showing its use.

Also mounted on the base are upwardly extending support members 12 and 13, on either side of the forehead rest. Forwardly extending arms 14 and 15, having keyhole-shaped rear plug portions 16 and 17, slideably engage vertically oriented slots in members 12 and 13. Channel 18 for receiving plug 16 is shown in FIG. 2. At the forward end of the arms are lateral flanges 21 and 22 which act as base members for rotatably mounted supports 23 and 24.

Each support 23 and 24 holds a device to support a lens for insertion and a suction member to remove lenses from the eye. The desired device may be moved into operating position simply by rotating the support until the insertion or removal device locks in place. If desired, rotation can be stopped at 90°, and neither device will be in operating position.

Extending upwardly from each support is a hollow flexible plastic tube, denoted by numerals 25 and 26, which is used to hold a lens for insertion in the eye. Each support also holds an upwardly oriented soft rubber suction cup, 32 and 34, mounted on vertical tubes 31 and 33, respectively. The tubes 31 and 33 extend from round metal plugs 29 and 30, which rest in depressions in the support. These plugs are easily removable for replacement or changing of suction members. Acrylic plastic dowel pins, shown in FIG. 3 as 53, are friction fitted into plastic tubes 31 and 33 to permit adequate suction to be obtained in cups 32 and 34 for lens removal. The plastic pins are transparent to permit passage of light for orientation of the user's head with respect to the cup. The insertion and removal devices are located on opposite sides of pivot points which allow the support to be rotated to move each device into position. As shown in FIG. 1, the apparatus is in an operating mode for insertion of lenses, with lenses 27 and 28 being depicted on the holding tubes.

Figure 3:
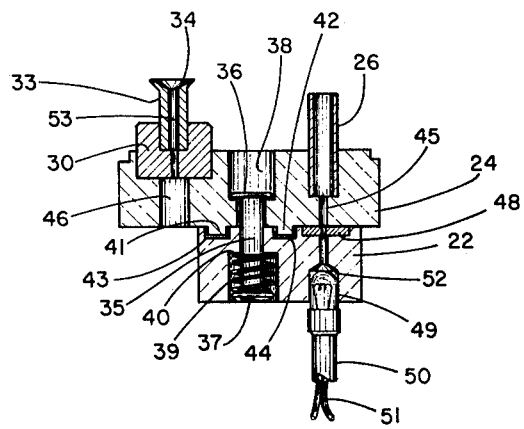
FIG. 3 is a partial section view of the rotatable lens support devices.
Figure 4:
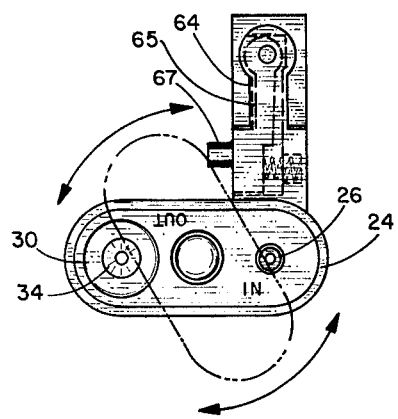
FIG. 4 is a partial top view showing the rotation of the lens supporting device.

A detailed section view of the rotatable supports is shown in FIG. 3. Support 24 is mounted above flange 22 and can rotate freely through a full 360° around cylindrical stud 35. The stud has round flanges 36 and 37 at opposing ends which act as stops to prevent movement of the stud through channel 38 in the support. Four downwardly extending teeth radially mounted at 90° intervals around bore 38 on the bottom of the support mate with depressions in the flange 22 to lock the support into place. Two of these teeth are shown at 41 and 42, with the corresponding depressions in the flange being shown as 43 and 44. Compression spring 39 acts between ledge 40 and flange 37 to urge the support toward the flange. The support is rotated by lifting it upwardly against the spring, thereby disengaging the teeth from the depressions, and permitting free rotation in either direction. When the desired orientation of the support is reached, the support is released, and the spring will draw the teeth back into the depressions and lock the support in place, with a substantially interocular distance between the two insertion (or removal) devices. Soft rubber support washer 48 mounts in a depression in flange 22 and extends slightly above the upper surface thereof to provide a cushion for support block 24. Rotation of the support is shown also in FIG. 4.

The user orients his eye relative to the insertion or removal devices by a beam of light which travels from a light source 49 through a bore 45 which extends through flange 22 and support 24, and through the orifice in tube 26 (or tube 33, depending on which is in operating position). The small light bulb rests in socket 50 and is electrically connected through wiring 51 through on-off toggle switch 55 to an electrical source. Ordinary household current is brought through cord 57 to plug 56 which mates with a receiving plug in the base. Electrical connections and the switch are housed in a small box 58. The light 49 fits slideably in an opening 52 in the bottom of the flange. A similar light (not shown) is located under the flange 21 on the right side of the apparatus and is electrically connected through cord 54.

A significant feature of the apparatus of the invention is its adjustability to adapt to the size and facial characteristics of virtually all users. The width between the left and right insertion/removal devices is adjustable, as is the height of each of the supports, and the distance between the forehead rest and the supports.

Figures 5, 6, 7:
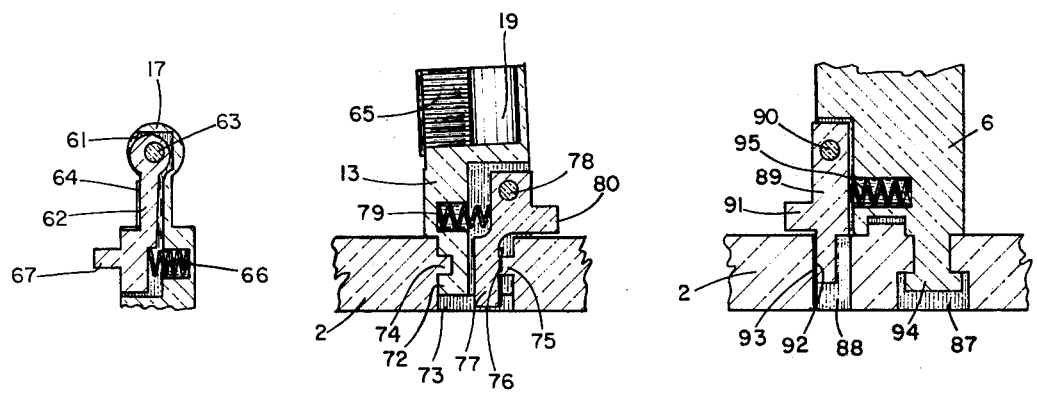
FIG. 5 is a top view of one of the vertical adjustments for the lens holding device.
FIG. 6 is a partial section side view showing the adjustment of the width between the lens supporting devices.
FIG. 7 is a partial section rear view showing the transverse adjustment of the forehead rest piece.

The mechanism of adjustment of the height of each of the support members is shown in FIGS. 2 and 5. A horizontal slot 61 in arm 17 contains a lever arm 62 mounted on pivot pin 63, which is oriented vertically in arm 17. The pivot pin is friction fit into a bore in the arm. A series of washboard-like ridges 64 extend along the side of the lever arm and mate with a corresponding series of ridges 65 on the inside of the sleeve 19 which receives the plug end of arm 17 (see FIGS. 4 and 6). The lever arm is actuated by pressing on boss 67 which compresses spring 66 and disengages ridges 64 from mating ridges 65, thereby permitting free sliding movement upwardly or downwardly of plug end of arm 17 in sleeve 19. When the desired level is obtained, pressure on the boss 67 is released and ridges 64 and 65 reengage, thereby locking the plug in place in the sleeve. The right support is independently adjustable in height as shown in FIG. 2. Lever arm 68 actuated by boss 69 permits plug 16 to move within sleeve 18. The level of adjustment is indicated by a scale 70 with graduated markings on arm 14.

The lateral adjustment of the width between the two support members is best shown in FIG. 6. A channel 73 extending along the width of the base has opposing elongated ribs 74 and 75. Rib 75 has a plurality of parallel vertical locking ridges 76 along its length. Support member 13 has a lower portion 72 adapted to slideably engage the ribs. A lever arm 77, moveable about pin 78 by urging boss 80 against spring 79, has a surface having vertical ridges which mate with the ridges 76. To move the supports inwardly or outwardly, the boss 80 is depressed and member 13 is moved accordingly. When the boss is released, the member is locked in position.

An identical mechanism for lateral adjustment of the right support is shown in FIG. 2. Lever arm 81, which pivots about pin 84, is actuated by pressing boss 83 against spring 82. Ridged surfaces on the lever arm and on the rib interlock at interface 86. A scale to indicate the extent of the adjustment is indicated at 85 in FIG. 1.

Backward and forward adjustment of the forehead rest is best illustrated in FIG. 7. Transverse slots 87 and 88 in base 2 receive a T-shaped guide piece 94 located at the bottom of vertical arm 6, and the lever arm 89, respectively. Lever arm 89 pivots around pin 80 and is actuated by pressing boss 91 which urges the lever arm against spring 95. This action disengages ridged surface 92 of the lever arm from corresponding surface 93 in slot 88, thereby allowing arm 13 to slide along the slot until the desired distance is reached.

It has been found that an important feature of the invention is the angle which the plane of the contact lens inserting or removing surface makes with respect to horizontal. This feature is best illustrated in FIG. 2. Forehead rest 7, arms 14 and 15, supports 23 and 24, and the plane of the upper edge of the circular surfaces of the insertion tube and the suction cup are all oriented at an angle of approximately 5° below horizontal. Note that the suction cup 32 and its metal holding device 29 have been removed in FIG. 2 for simplicity of viewing. The angle of inclination of the upper portions of the device is preferably maintained between about 3 and about 10°. The angling of the device appears to greatly facilitate both insertion and removal of the lenses, particularly the latter.

Operation of the apparatus of the invention is quite simple. For insertion of lenses, the user orients the supports as shown in FIG. 1, places wetting solution on the lenses, and places the lenses on the vertical insertion tubes as shown in FIG. 1. The lights in each flange 21 and 22 are then turned on by toggle switch 55, thereby sending a beam of light through the insertion tubes. The user then rests his forehead against the surface 8 of arm 7, and, keeping his eye open, moves his eyes downwardly toward the lenses. As the downward motion continues, flanges 10 and 11 will press against his upper eyelids, thereby maintaining the lids in a wide-open position. The user then continues to move his eyes slowly toward the dots of light until the eyes touch the lenses. Because of surface tension between the liquid in the eye and the liquid on the lens, the lens will quickly slide into proper place in the eye.

For removing the lenses, the support members are lifted and rotated to bring suction cups into operating position. Since the insertion tube and suction cup are located equidistant from the point of rotation of the support member, no further adjustment in distance between the support members should be necessary. The user repeats the process, placing his forehead on the forehead rest surface and bringing his eyes toward the suction cups by following the lights therein. Because of the slight angularity of the plane of the suction cup, the upper portion of the suction cup will first contact the upper portion of the lens, placing slight pressure on the lens and tending to release the bottom of the lens from the eye. At this point the lens is in contact with the suction cup and is quickly and easily removed from the eye.

When it is desired to insert or remove only one lens at a time, the support not desired to be used can be rotated 90° and locked into position. This orientation precludes either the insertion or removal device for interfering.

The units can be made from any structural material, but are preferably fabricated from plastic such as acrylic. The component parts can easily be injection molded, for example, from polystyrene or polyethylene. While the invention has been described with respect to a specific example thereof, many modifications and variations of the specific design are possible within the scope and spirit of the invention, which should be considered limited only by the following claims.

I claim:

1. Apparatus for inserting and/or removing contact lenses comprises a base, forehead rest means for receiving and supporting the forehead of a user in a downwardly facing position, a pair of lens resting means for holding a contact lens in a substantially horizontal plane for insertion, mounting means for each of said lens resting means for removing said lens resting means between an operative position and an inoperative position, and a pair of lid-opening means mounted between the forehead rest means and the lens resting means.

2. The apparatus of claim 1 also comprising a pair of lens removing means for removal of a contact lens from an eye of a user.

3. The apparatus of claim 2 also comprising mounting means for each of said lens removing means for moving said lens removing means between an operative position and an inoperative position.

4. The apparatus of claim 2 wherein the lens removing means comprise flexible suction cups, and the apparatus also comprises mounting means for maintaining the suction cup at an angle of from about 3° to about 10° from horizontal.

5. The apparatus of claim 1 also comprising a pair of support members mounted on the base, each support member having thereon a lens resting means and a separate lens removing means for removal of a contact lens from an eye of a user, mounting means for each support member for selectively moving the lens resting means and the lens removing means between an operative position and an inoperative position.

6. The apparatus of claim 5 wherein the support members are rotatably mounted in a substantially horizontal plane, and the apparatus comprises a source of illumination, and a light passageway to selectively direct illumination from said source through the lens resting means and the lens removing means when the lens resting means or lens removing means is in operative position.

7. The apparatus of claim 1 having adjustment means for varying the distance between the lens resting means when they are in operative position.

8. The apparatus of claim 1 also comprising adjustable mounting means for the forehead rest means for varying the position of the forehead rest means on the base relative to the position of the lens resting means.

9. The apparatus of claim 1 having adjustable mounting means for each lens resting means for independently varying the height of each lens resting means above the base.

* * * * *